(12) United States Patent
Elomari et al.

(10) Patent No.: US 9,115,326 B2
(45) Date of Patent: *Aug. 25, 2015

(54) MONOESTER-BASED LUBRICANTS AND METHODS OF MAKING SAME

(71) Applicant: Chevron U.S.A. Inc., San Ramon, CA (US)

(72) Inventors: Saleh Ali Elomari, Fairfield, CA (US); Stephen Joseph Miller, San Francisco, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/279,027

(22) Filed: May 15, 2014

(65) Prior Publication Data

US 2014/0249062 A1  Sep. 4, 2014

Related U.S. Application Data

(60) Provisional application No. 13/682,542, filed on Nov. 20, 2012.

(51) Int. Cl.
*C10M 105/34* (2006.01)
*C10M 129/95* (2006.01)
(Continued)

(52) U.S. Cl.
CPC .............. *C10M 105/34* (2013.01); *C07C 69/24* (2013.01); *C10M 129/70* (2013.01);
(Continued)

(58) Field of Classification Search
CPC ............. C10M 105/34; C10M 129/70; C10M 2203/1025; C10M 2203/1006; C10M 2207/281; C07C 69/24; C10N 2270/00; C10N 2230/10; C10N 2220/023; C10N 2230/02; C10N 2220/022
See application file for complete search history.

(56) References Cited

U.S. PATENT DOCUMENTS 2,510,300 A  6/1950  Walls
2,797,196 A  6/1957  Dunn et al.
(Continued)

FOREIGN PATENT DOCUMENTS

CN  103789070 A  5/2014
EP  0374671  6/1990
(Continued)

OTHER PUBLICATIONS

International Search Report from corresponding PCT Application PCT/US2014/038252 mailed Feb. 11, 2015.
(Continued)

*Primary Examiner* — Pamela H Weiss
(74) *Attorney, Agent, or Firm* — Melissa M. Hayworth; Steven H. Roth; Mary R. Bram

(57) ABSTRACT

Disclosed herein are monoester-based lubricant compositions and methods of making these monoester-based lubricant compositions. The monoester lubricant compositions comprise an isomeric mixture of at least one monoester species having a carbon number ranging from $C_8$ to $C_{40}$. In some embodiments, the methods for making the monoester-based lubricants utilize a biomass precursor and/or low value Fischer-Tropsch (FT) olefins and/or alcohols to produce high value monoester-based lubricants. In some embodiments, the monoester-based lubricants are derived from FT olefins and fatty acids. The fatty acids can be from a bio-based source (i.e., biomass, renewable source) or can be derived from FT alcohols via oxidation.

14 Claims, 6 Drawing Sheets

Internal (secondary) monoesters

(51) Int. Cl.
*C07C 69/24* (2006.01)
*C10M 129/70* (2006.01)

(52) U.S. Cl.
CPC ............... *C10M 2203/1006* (2013.01); *C10M 2203/1025* (2013.01); *C10M 2207/2815* (2013.01); *C10N 2220/023* (2013.01); *C10N 2230/02* (2013.01); *C10N 2230/10* (2013.01); *C10N 2270/00* (2013.01)

(56) References Cited

U.S. PATENT DOCUMENTS

| | | | |
|---|---|---|---|
| 2,936,856 | A | 5/1960 | Braunwarth et al. |
| 5,091,270 | A * | 2/1992 | Ohya et al. ............... 428/843.4 |
| 5,232,910 | A | 8/1993 | Mueller |
| 5,252,554 | A | 10/1993 | Mueller |
| 5,318,954 | A | 6/1994 | Mueller et al. |
| 5,403,822 | A | 4/1995 | Mueller et al. |
| 5,441,927 | A | 8/1995 | Mueller et al. |
| 6,008,167 | A | 12/1999 | Appelman et al. |
| 6,100,223 | A * | 8/2000 | Gee ............... 507/267 |
| 6,191,076 | B1 * | 2/2001 | Gee ............... 507/267 |
| 6,281,404 | B1 | 8/2001 | Miller |
| 6,667,285 | B1 * | 12/2003 | Kawahara et al. ............ 508/485 |
| 6,849,581 | B1 | 2/2005 | Thompson et al. |
| 7,008,909 | B2 * | 3/2006 | Burgo et al. ............... 508/463 |
| 7,666,820 | B2 | 2/2010 | Mueller et al. |
| 8,148,305 | B2 | 4/2012 | Westfechtel et al. |
| 8,153,562 | B2 | 4/2012 | Muller et al. |
| 8,236,735 | B2 | 8/2012 | Maker et al. |
| 2003/0114316 | A1 | 6/2003 | Patel et al. |
| 2005/0239662 | A1 | 10/2005 | Patel |
| 2006/0019840 | A1 * | 1/2006 | Kawahara et al. ............ 508/280 |
| 2006/0073981 | A1 | 4/2006 | Gee |
| 2006/0254826 | A1 | 11/2006 | Alberthy |
| 2007/0219097 | A1 | 9/2007 | Mueller et al. |
| 2010/0261627 | A1 | 10/2010 | Miller et al. |
| 2011/0009300 | A1 | 1/2011 | Elomari et al. |
| 2012/0053099 | A1 | 3/2012 | Zhou et al. |
| 2012/0329682 | A1 | 12/2012 | Fefer |
| 2013/0085090 | A1 * | 4/2013 | Kim et al. ............... 508/404 |

FOREIGN PATENT DOCUMENTS

| | | |
|---|---|---|
| EP | 0374672 | 6/1990 |
| EP | 0374672 | 6/2009 |
| GB | 732376 * | 12/1951 |
| WO | WO 9530818 A1 * | 11/1995 |
| WO | 9933932 | 7/1999 |
| WO | 9936387 | 7/1999 |
| WO | 2007137709 | 12/2007 |
| WO | 2008046554 | 4/2008 |
| WO | 2009053455 | 4/2009 |
| WO | 2009130445 A1 | 10/2009 |
| WO | 2009142922 | 11/2009 |

OTHER PUBLICATIONS

Sheldon R.A., Kochi J.K., Metal-Catalyzed Oxidations of Organic Compounds, Mechanistic Principles and Synthetic Methodology Including Biochemical Processes, 1981, Academic Press, pp. 295-297 and 162-171.

Schroder M., Osmium Tetraoxide Cis Hydroxylation of Unsaturated Substrates, Chem. Rev., 1980, 80, 1878-213.

Munch-Petersen J., 3-Methylheptanoic Acid, Organic Synthesis, Coll. vol. 5, p. 762 (1973); vol. 41, p. 60 (1961).

Spangler F.W., Allen C.F.R., y-Chloropropyl Acetate, Organic Synthesis, Coll. vol. 3, p. 203 (1955); vol. 29, p. 33 (1940).

Swern D., Findley T.W., and Scanian J.T., Epoxidation of Oleic Acid, Methyl Oleate and Oleyl Alcohol with Perbenzoic Acid, J. Am. Chem. Soc., 1944, 66 (11), 192501927.

* cited by examiner

Internal (secondary) monoesters a representation of octylhexanoate monoesters a representation of decylhexanoate monoesters Octenes Epoxidation
mCPBA Epoxy Octenes

MONOESTER-BASED LUBRICANTS AND METHODS OF MAKING SAME

RELATED PRIOR APPLICATIONS

This application is a Continuation-In-Part of U.S. patent application Ser. No. 13/682,542 filed Nov. 20, 2012, entitled "Monoester-Based Lubricants and Methods of Making Same", the entire disclosure of which is herein incorporated by reference.

FIELD OF THE INVENTION

This invention relates to ester-based lubricants, and specifically to monoester-based lubricants, and methods of making them.

BACKGROUND OF THE INVENTION

Esters have been used as lubricating oils for over 50 years. They are used in a variety of applications ranging from jet engines to refrigeration, including drilling fluid. In fact, esters were the first synthetic crankcase motor oils in automotive applications. Esters, however, gave way to polyalphaolefins (PAOs) due to the lower cost of PAOs and their formulation similarities to mineral oils. In full synthetic motor oils, however, esters are almost always used in combination with PAOs to balance the effect on seals, additives solubility, volatility reduction, and energy efficiency improvement by enhanced lubricity.

Ester-based lubricants, in general, have excellent lubrication properties due to the polarity of the ester molecules of which they are comprised. The polar ester groups of such molecules strongly adhere to metal surfaces creating protective films which slow down the wear and tear of the metal surfaces. Such lubricants are less volatile than the traditional lubricants and tend to have much higher flash points and much lower vapor pressures. Ester lubricants are excellent solvents and dispersants, and can readily solvate and disperse the degradation by-products of oils. Therefore, they greatly reduce sludge buildup. While ester lubricants are stable to thermal and oxidative processes, the ester functionalities give microbes a means to do their biodegrading more efficiently and more effectively than their mineral oil-based analogues. However, the preparation of esters is more involved and can be more costly than the preparation of their PAO counterparts.

In view of the foregoing, a simpler, more efficient method of generating ester-based lubricants would be extremely useful—particularly wherein such methods utilize renewable raw materials in combination with converting low value Fischer-Tropsch (FT) olefins and alcohols to high value ester lubricants.

BRIEF DESCRIPTION OF THE INVENTION

The present invention is generally directed to monoester-based lubricant compositions. The present invention is also directed to methods of making these and other similar lubricant compositions. In some embodiments, the methods for making such monoester-based lubricants utilize a biomass precursor. In these or other embodiments, lubricant precursor species can also be sourced or derived from Fischer-Tropsch (FT) reaction products.

In some embodiments, the present invention is directed to lubricant compositions comprising an isomeric mixture of at least one monoester species, the monoester species having the structures depicted in FIG. 2 wherein $R_1$, $R_2$, and $R_3$, are independently selected from alkyl groups to form an isomeric mixture of monoesters with a total carbon number ranging from 8 to 40. As such, $R_1$, $R_2$, and $R_3$, are selected from alkyl groups and may be the same or different. In one embodiment, the lubricant composition comprises an isomeric mixture of at least one monoester species having a total carbon number ranging from 10 to 24. In another embodiment, the monoester species has a total carbon number ranging from 12 to 18 and in yet another embodiment, the monoester species has a total carbon number ranging from 12 to 16.

In one embodiment, the present invention is directed to processes comprising the steps of (a) isomerizing alpha olefins to provide an isomeric mixture of internal olefins; (b) epoxidizing internal olefins from step (a) to provide internal epoxides; (c) opening the epoxide rings of the epoxides of step (b) by reduction providing secondary alcohols; (d) esterifying the secondary alcohols of step (c) with a $C_2$ to $C_{18}$ carboxylic acid to provide an isomeric mixture of at least one monoester species; and (e) isolating the isomeric mixture of at least one monoester species having viscosity and pour point suitable for use as a lubricant.

In certain embodiments, the alpha olefins can be derived from a Fischer-Tropsch process. In these other embodiments, the $C_2$ to $C_{18}$ carboxylic acid can be derived from a Fischer-Tropsch process or from a bio-derived fatty acid.

In certain embodiments, the present invention is directed to processes comprising the steps of (a) isomerizing an alpha olefin or mixture of alpha olefins having a carbon number from 6-22 to an isomeric mixture of internal olefins (b) epoxidizing the isomeric mixture of internal olefins having a carbon number of from 6 to 22 to form an isomeric mixture of internal epoxides comprising an epoxide ring; (c) opening the epoxide rings by reduction to form an isometric mixture of secondary alcohols; (d) esterifying the isomeric mixture of secondary alcohols with a $C_2$ to $C_{18}$ carboxylic acids or their acylating derivatives such as acyl chloride or anhydrides to form an isomeric mixture of internal (secondary) at least one monoester species; and (e) isolating the isomeric mixture of at least one monoester species having viscosity and pour point suitable for use as a lubricant. The carboxylic acids or their acylating derivatives such as acyl chloride or anhydrides can be derived from a Fischer-Tropsch process or from a bio-derived fatty acid. The alpha olefins can be derived from a Fischer-Tropsch process.

In other embodiments, the present invention is directed to processes comprising the steps of: (a) isomerizing a plurality of alpha olefins having a carbon number from 6-22 to provide an isomeric mixture of a plurality of internal olefins b) epoxidizing the isomeric mixture of internal olefins to form an isomeric mixture of a plurality of internal epoxides; (c) converting the isomeric mixture of internal epoxides to an isomeric mixture of a plurality of secondary alcohols; (d) esterifying the isomeric mixture of secondary alcohols with a $C_2$ to $C_{18}$ esterifying species to form an isomeric mixture of a plurality of internal monoesters; and (e) isolating the isomeric mixture of a plurality of monoester species having viscosity and pour point suitable for use as a lubricant. In certain embodiments the esterifying species can be carboxylic acids or their acylating derivatives, such as acyl chloride or anhydrides, derived from a Fischer-Tropsch process or from a bio-derived fatty acid. In these and other embodiments, the alpha olefins can be derived from a Fischer-Tropsch process.

The olefins disclosed here may be alpha olefins produced by gas to liquid processes (GTL), refining processes, petrochemical processes, pyrolysis of waste plastics and other processes. The alpha olefins are isomerized to provide an isomeric mixture of internal olefins, and this isomeric mixture of internal olefins is converted into monoesters. The alpha olefins are isomerized into internal olefins using double bond isomerization catalysts, including silicoaluminophosphates molecular sieves such as SAPO-39 and medium pore aluminosilicates zeolites, such as SSZ-32 and ZSM-23.

The monoesters produced from the internal olefins are a mixture of isomers and possess superior oxidative and hydrolytic stability. Such isomeric mixtures of these monoesters also have low temperature properties that are desirable, such as lower cloud points and pour points. This results from inhibition in crystal formation due to the presence of the mixture of isomers of monoesters.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings.

DETAILED DESCRIPTION OF THE INVENTION

1. Introduction

Figure 1:
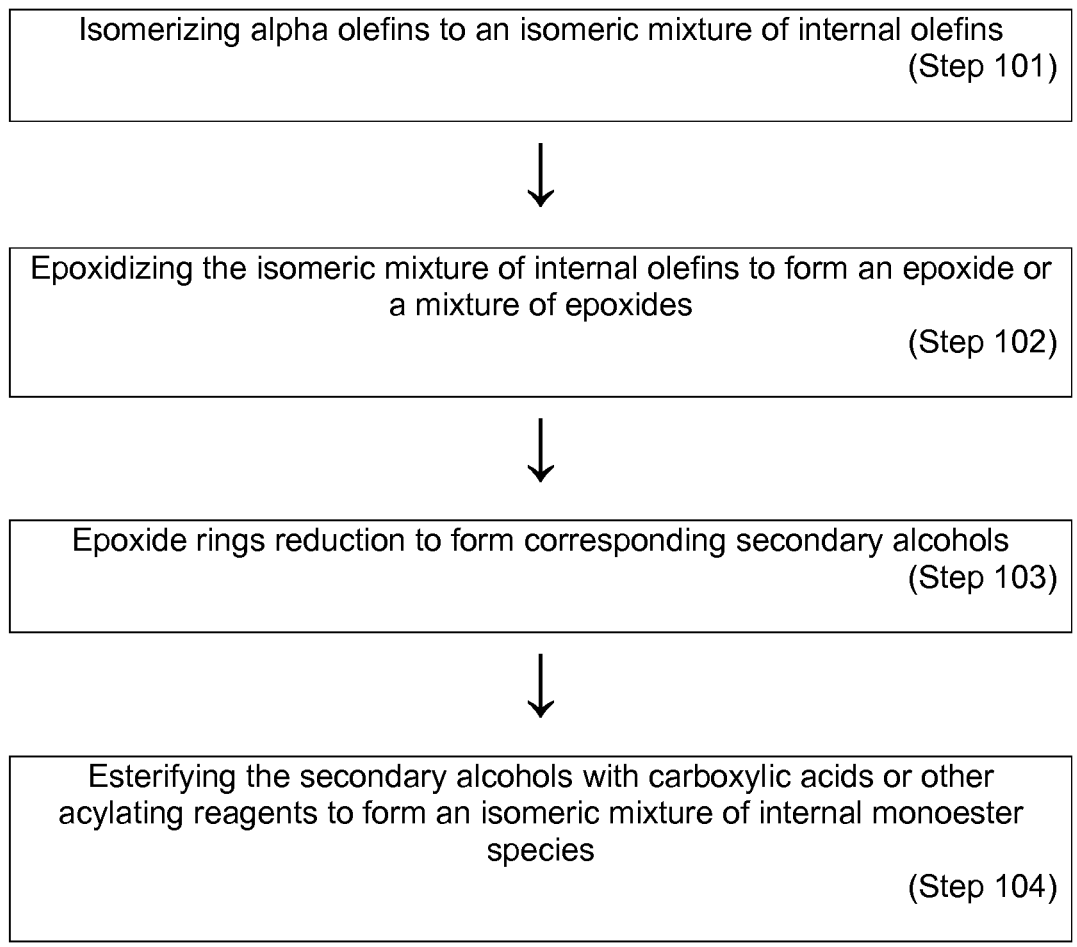
FIG. 1 is a flow diagram illustrating a method of making monoester based lubricant composition, in accordance with certain embodiments of the present invention.

The present invention is directed to monoester-based lubricant compositions comprising an isomeric mixture of at least one monoester species. The present invention is also directed to methods of making these and other similar lubricant compositions. In some embodiments, the methods for making such monoester-based lubricants utilize a biomass precursor and/or low value Fischer-Tropsch (FT) olefins and/or alcohols so as to produce high value monoester-based lubricants. In some embodiments, such monoester-based lubricants are derived from FT olefins and fatty (carboxylic) acids. In these or other embodiments, the fatty acids can be from a bio-based source (i.e., biomass, renewable source) or can be derived from FT alcohols via oxidation.

Because biolubricants and biofuels are increasingly gaining ground and becoming topics of focus for many in the oil industry, the use of biomass in the making of such above-mentioned lubricants could be attractive from several different perspectives. To the extent that biomass is so utilized in making the monoester-based lubricants of the present invention, such lubricants are deemed to be biolubricants.

2. Definitions

"Lubricants," as defined herein, are substances (usually a fluid under operating conditions) introduced between two moving surfaces so to reduce the friction and wear between them. Base oils used as motor oils are generally classified by the American Petroleum Institute as being mineral oils (Group I, II, and III) or synthetic oils (Group IV and V). See American Petroleum Institute (API) Publication Number 1509.

"Pour point," as defined herein, represents the lowest temperature at which a fluid will pour or flow. See, e.g., ASTM International Standard Test Methods D 5950-96, D 6892-03, and D 97.

"Cloud point," as defined herein, represents the temperature at which a fluid begins to phase separate due to crystal formation. See, e.g., ASTM Standard Test Methods D 5773-95, D 2500, D 5551, and D 5771.

The Oxidator BN test referred to herein is a test measuring resistance to oxidation by means of a Dornte-type oxygen absorption apparatus (R. W. Dornte "Oxidation of White Oils," Industrial and Engineering Chemistry, Vol. 28, page 26, 1936). Normally, the conditions are one atmosphere of pure oxygen at 340° F., and one reports the hours to absorption of 1000 ml of $O_2$ by 100 g. of oil. In the Oxidator BN test, 0.8 ml of catalyst is used per 100 grams of oil and an additive package is included in the oil. The catalyst is a mixture of soluble metal-naphthenates simulating the average metal analysis of used crankcase oil. The additive package is 80 millimoles of zinc bispolypropylenephenyldithiophosphate per 100 grams of oil. The Oxidator BN measures the response of a lubricating oil in a simulated application. High values, or long times to adsorb one liter of oxygen, indicate good stability.

"Centistoke," abbreviated "cSt," is a unit for kinematic viscosity of a fluid (e.g., a lubricant), wherein 1 centistoke equals 1 millimeter squared per second (1 cSt=1 $mm^2/s$). See, e.g., ASTM Standard Guide and Test Methods D 2270-04, D 445-06, D 6074, and D 2983.

"Alkyl groups" are straight-chain or branched-chain monovalent hydrocarbon radicals containing from 1 to 40 carbon atoms. Examples of alkyl groups include methyl, ethyl, n-propyl, n-butyl, isopropyl, tert-butyl, hexyl, octyl, and the like. As defined herein, $R_1$, $R_2$, and $R_3$ are independently selected from alkyl groups and as such, $R_1$, $R_2$, and $R_3$ can be the same or different alkyl groups.

With respect to describing molecules and/or molecular fragments herein, "$R_n$," where "n" is an index, refers to a hydrocarbon group, wherein the molecules and/or molecular fragments can be linear and/or branched. As defined herein, "$C_n$," where "n" is an integer, describes a hydrocarbon molecule or fragment (e.g., an alkyl group) wherein "n" denotes the number of carbon atoms in the fragment or molecule.

The prefix "bio," as used herein, refers to an association with a renewable resource of biological origin, such as resource generally being exclusive of fossil fuels.

The term "internal olefin," as used herein, refers to an olefin (i.e., an alkene) having a non-terminal carbon-carbon double bond (C═C). This is in contrast to "α-olefins" which do bear a terminal carbon-carbon double bond.

"Isomers" and "isomeric mixtures" as used herein include compounds with the same chemical formula but a different arrangement of atoms. Accordingly, the isomeric mixture of a monoester species includes compounds with the same chemical formula and thus the same carbon number, but with the ester moiety attached at different positions along the carbon chain and with different branching within the carbon chain.

The term "isomeric mixture" as used herein, means a composition comprising more than one isomer of a monoester species. The "monoester species" is a monoester of a single carbon number. The isomers of a monoester species have the same chemical formula and thus the same carbon number, but with the ester moiety attached at different positions along the carbon chain and with different branching within the carbon chain. For example, an isomeric mixture of a single monoester species includes hexanyl octanoate and its isomers (the isomers having the ester moiety attached at different positions along the carbon chain and with different branching within the carbon chain).

The "isomeric mixture of at least one monoester species" optionally contains isomers of more than one monoester. As such, the isomeric mixture contains more than one (i.e., two or more) isomers of a single monoester species and also can contain isomers of more than one (i.e., two or more) different monoester species. Different monoester species have different chemical formula and thus different carbon number. For example, an isomeric mixture of at least one monoester species includes hexanyl octanoate and its isomers and hexanyl octanoate and its isomers and hexanyl decanoate and its isomers (the isomers having the ester moiety attached at different positions along the carbon chain and with different branching within the carbon chain).

These isomeric mixtures as disclosed herein are distinguished from single monoester compounds.

3. Monoester Lubricant Compositions

Figure 2A:
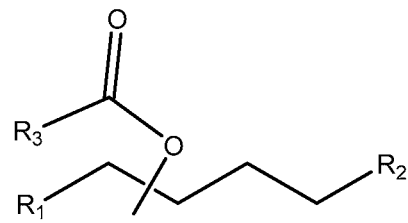
FIG. 2(A) is a diagram of a generic monoester.
Figure 2B:
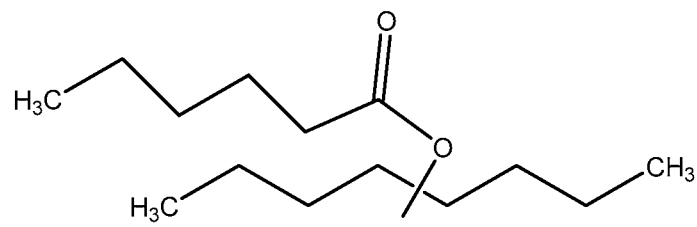
FIG. 2(B) illustrates a octyl hexanoate.
Figure 2C:
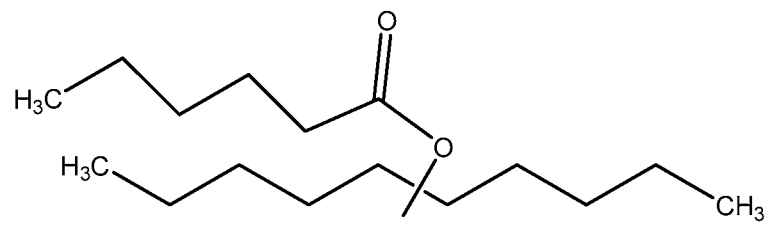
FIG. 2(C) illustrates a decyl hexanoate, two exemplary monoester-based compounds suitable for use as lubricants in accordance with some embodiments of the present invention.

In some embodiments, the present invention is directed to monoester based lubricant compositions comprising an isomeric mixture of at least one monoester species. The isomeric mixture of the monoester species has a chemical structure as depicted in FIG. 2, wherein $R_1$, $R_2$, and $R_3$, are independently selected from alkyl groups to form an isomeric mixture of monoesters with a total carbon number ranging from 8 to 40. As such, $R_1$, $R_2$, and $R_3$, are independently selected from alkyl groups and can be the same or different. In one embodiment, the lubricant composition comprising an isomeric mixture of at least one monoester species, the monoester species has a total carbon number ranging from 10 to 24. In another embodiment, the isomeric mixture of at least one monoester species has a total carbon number ranging from 12 to 18 and in yet another embodiment, the isomeric mixture of at least one monoester species has a total carbon number ranging from 12 to 16.

In one embodiment, $R_1$ and $R_2$ are derived from an isomeric mixture of olefins and $R_3$ is derived from a carboxylic acid. In certain embodiments, the total carbon number of the parent olefin utilized in the synthesis of the monoester species ranges from $C_6$ to $C_{22}$ and the total carbon number of the parent carboxylic acid utilized in the synthesis of the monoester species (providing $R_3$) ranges from $C_2$ to $C_{18}$.

The resulting isomeric mixture of at least one monoester species as described herein has a total carbon number ranging from 8 to 40. As described herein, this isomeric mixture can contain isomers of one monoester species, as well as isomers of multiple monoester species. $R_1$, $R_2$, and $R_3$, are independently selected from alkyl groups to provide the described monoester species. In one embodiment, the isomeric mixture of at least one monoester species has a total carbon number ranging from 10 to 24. In another embodiment, the isomeric mixture of at least one monoester species has a total carbon number ranging from 12 to 18, and in yet another embodiment, the at least one monoester species has a total carbon number ranging from 12 to 16.

Regarding the above-mentioned monoester species, selection of $R_1$, $R_2$, and $R_3$ can follow any or all of several criteria. For example, in some embodiments, $R_1$, $R_2$, and $R_3$ are selected such that the kinematic viscosity of the composition of the monoesters at a temperature of 100° C. is typically in the range from 0.5 centistokes to 2.0 centistokes. In some or other embodiments, $R_1$, $R_2$, and $R_3$ are selected such that the pour point of the resulting lubricant is −20° C. or lower. In certain embodiments the pour point of the resulting lubricant is −20° C. to −60° C. or lower. The monoester species as described herein can have a pour point of −20° C. or lower and in certain embodiments, −60° C. or lower. In some embodiments, $R_1$, $R_2$, and $R_3$ are selected such that the resulting lubricant exhibits an Oxidator BN value of from about 25 hours to about 65 hours.

In some embodiments, $R_1$ and $R_2$ are selected to have a combined carbon number (i.e., total number of carbon atoms) of from 6 to 22. The other embodiments, $R_1$ and $R_2$ are selected to provide a combined carbon number of $C_4$ to $C_{14}$. In yet other embodiments, $R_1$ and $R_2$ are selected to provide a combined carbon number of $C_4$ to $C_8$. In these or other embodiments, $R_3$ is selected to have a carbon number of from $C_2$ to $C_{18}$. In certain embodiments, $R_3$ is selected to have a carbon number of from $C_5$ to $C_{14}$ or $C_5$ to $C_{10}$. Depending on the embodiment, such resulting monoester species can have a molecular mass between 144 atomic mass units (a.m.u.) and 592 a.m.u.

In some embodiments, the above-described compositions are substantially homogeneous in terms of their monoester component and as such, primarily contain isomers of one monoester. In other embodiments, the monoester component comprises a variety (i.e., a mixture) of monoester species, and as such, contains isomers of a variety of monoesters. When the compositions comprise isomers of a variety of monoesters, the compositions contain isomers of 2 or more monoester species. In some embodiments, the compositions comprise isomers of 1 to 100 monoesters. In some embodiments, the compositions comprise isomers of 1 to 70 monoesters. In other embodiments, the compositions comprise isomers of 1 to 50 monoesters. In yet other embodiments, the compositions comprise isomers of 1 to 20 monoesters. In certain other embodiments, the compositions comprise isomers of 1 to 10 monoesters.

In some embodiments, the monoester-based lubricant composition comprises an isomeric mixture of at least one monoester species derived from a $C_6$ to $C_{22}$ olefin and a $C_2$ to $C_{18}$ carboxylic acid. Typically, the monoester species are made by reacting —OH groups (of secondary alcohols) with a carboxylic acid of a different carbon number. The monoester species also can be made by esterification of secondary alcohols with a carboxylic acid of the same carbon number.

In some of the above described embodiments, the olefins used in making the precursor secondary alcohols can be one of the following olefins: hexenes, heptenes, octenes, nonenes, decenes, undecenes, dodecenes, tridecenes, tetradecenes, pentadecenes, hexadecenes, hepta decenes, octadecenes, nona-decenes, icosenes, henicosenes and docosenes or mixtures thereof.

In some of the described embodiments, the carboxylic acids used in making the monoester species are selected from the group consisting of propionic acid, butyric acid, petanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, octadecanoic acid or mixtures thereof.

In some of the above-described embodiments, the monoester-based lubricant composition comprises an isomeric mixture of at least one monoester species selected from the group consisting of hexanyl propanoate and isomers, hexanyl butyrate and isomers, hexanyl hexanoate and isomers, hexanyl octanoate and isomers, hexanyl decanoate and isomers, hexanyl laureate and isomers, hexanyl palmitate and isomers, hexanyl hexadecanoate and isomers, hexanyl stearate and isomers, octanyl propanoate and isomers, octanyl butyrate and isomers, octanyl hexanoate and isomers, octanyl octanoate and isomers, octanyl decanoate and isomers, octanyl laureate and isomers, octanyl palmitate and isomers, octanyl hexadecanoate and isomers, octanyl stearate and isomers, decanyl propanoate and isomers, decanyl butyrate and isomers, decanyl hexanoate and isomers, decanyl octanoate and isomers, decanyl decanoate and isomers, decanyl laureate and isomers, decanyl palmitate and isomers, decanyl hexadecanoate and isomers, decanyl stearate and isomers, dodecanyl propanoate and isomers, dodecanyl butyrate and isomers, dodecanyl hexanoate and isomers, dodecanyl octanoate and isomers, dodecanyl decanoate and isomers, dodecanyl laureate and isomers, dodecanyl palmitate and isomers, dodecanyl hexadecanoate and isomers, dodecanyl stearate and isomers, tetradecanyl propanoate and isomers, tetradecanyl butyrate and isomers, tetradecanyl hexanoate and isomers, tetradecanyl octanoate and isomers, tetradecanyl decanoate and isomers, tetradecanyl laureate and isomers, tetradecanyl palmitate and isomers, tetradecanyl hexadecanoate and isomers, tetradecanyl stearate and isomers, hexadecanyl propanoate and isomers, hexadecanyl butyrate and isomers, hexadecanyl hexanoate and isomers, hexadecanyl octanoate and isomers, hexadecanyl decanoate and isomers, hexadecanyl laureate and isomers, hexadecanyl palmitate and isomers, hexadecanyl hexadecanoate and isomers, hexadecanyl stearate and isomers, octadecanyl propanoate and isomers, octadecanyl butyrate and isomers, octadecanyl hexanoate and isomers, octadecanyl octanoate and isomers, octadecanyl decanoate and isomers, octadecanyl laureate and isomers, octadecanyl palmitate and isomers, octadecanyl hexadecanoate and isomers, octadecanyl stearate and isomers, icosanyl propanoate and isomers, icosanyl butyrate and isomers, icosanyl hexanoate and isomers, icosanyl octanoate and isomers, icosanyl decanoate and isomers, icosanyl laureate and isomers, icosanyl palmitate and isomers, icosanyl hexadecanoate and isomers, icosanyl stearate and isomers, docosanyl propanoate and isomers, docosanyl butyrate and isomers, docosanyl hexanoate and isomers, docosanyl octanoate and isomers, docosanyl decanoate and isomers, docosanyl laureate and isomers, docosanyl palmitate and isomers, docosanyl hexadecanoate and isomers, docosanyl stearate and isomers, and mixtures thereof.

In some embodiments, the monoester-based lubricant composition further comprises a base oil selected from the group consisting of Group I oils, Group II oils, Group III oils, and mixtures thereof.

It is worth noting that in most applications, the above-described esters and their compositions are unlikely to be used as lubricants by themselves, but are usually used as blending stocks. As such, esters with higher pour points may be used as blending stocks with other lubricant oils since they are very soluble in hydrocarbons and hydrocarbon-based oils.

When blended with a base oil, the monoester-based lubricant composition may comprise from about 5 to about 50 wt % of the isomeric mixture of at least one monoester species.

4. Methods of Making Monoester Lubricants

As mentioned above, the present invention is additionally directed to methods of making the above-described lubricant compositions comprising a mixture of isomers of at least one monoester species.

Referring to the flow diagram shown in FIG. 1, in some embodiments, processes for making the above-mentioned monoester species, typically having lubricating base oil viscosity and pour point, comprise the following steps: (Step 101) isomerizing alpha olefins to an isomeric mixture of internal olefins; (Step 102) epoxidizing the isomeric mixture of internal olefins having a carbon number of from 6 to 22 to form an epoxide or a mixture of epoxides; (Step 103) opening the epoxide rings by reduction methods to form the corresponding mono secondary alcohols; and (Step 104) esterifying (i.e., subjecting to esterification) the secondary alcohols with a $C_2$ to $C_{18}$ carboxylic acid to form an isomeric mixture of internal monoester species. Generally, lubricant compositions comprising such monoester species have a viscosity in the range from 0.5 centistokes to 2 centistokes at a temperature of 100° C.

In some embodiments, the monoester species formed can be substantially homogeneous and as such, the compositions primarily contain isomers of one monoester species. In other embodiments, the monoester species formed comprises a variety (i.e., a mixture) of monoester species, and as such, the compositions contain isomers of two or more monoesters. In some embodiments, the compositions comprise isomers of 1 to 100 monoesters. In other embodiments, the compositions comprise isomers of 1 to 20 monoesters.

In some of the above-described method embodiments, the olefin used is a reaction product of a Fischer-Tropsch process. In these or other embodiments, the carboxylic acid can be derived from alcohols generated by a Fischer-Tropsch process and/or the carboxylic acid can be a bio-derived fatty acid.

In some embodiments, the olefin is an α-olefin (i.e., an olefin having a double bond at a chain terminus). In these embodiments, it is usually necessary to isomerize the olefin so as to internalize the double bond. This isomerization is typically carried out catalytically using a catalyst including, but not limited to, crystalline aluminosilicate and like materials and aluminophosphates. See, e.g., U.S. Pat. Nos. 2,537,283; 3,211,801; 3,270,085; 3,327,014; 3,304,343; 3,448,164; 4,593,146; 3,723,564 and 6,281,404. U.S. Pat. No. 6,281,404 claims a crystalline aluminophosphate-based catalyst with 1-dimensional pores of size between 3.8 Å and 5 Å.

Figure 3:
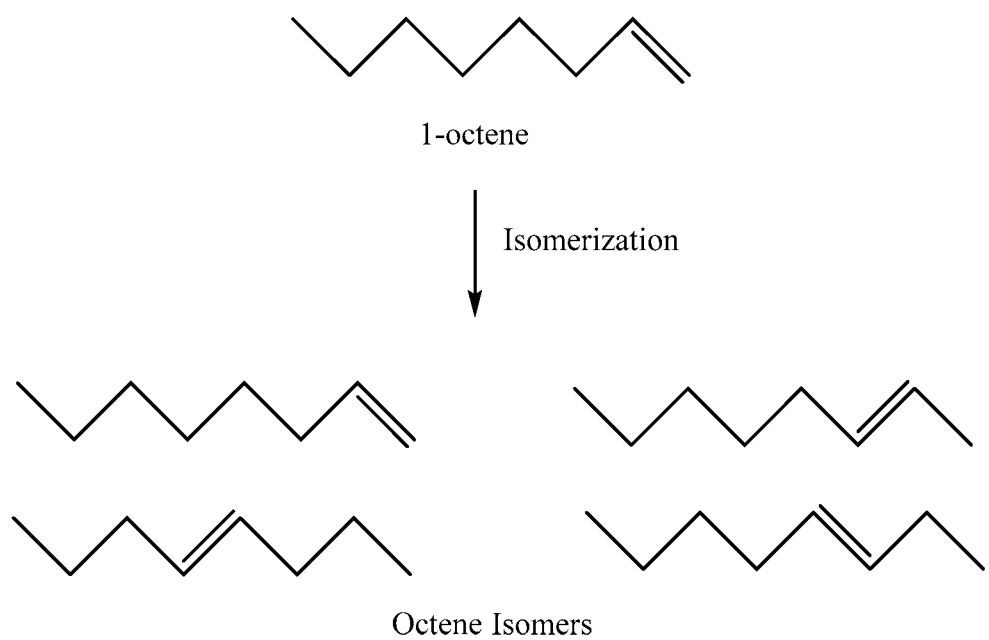
FIG. 3 (Scheme 1) is a chemical flow diagram illustrating isomerization of alpha olefins to internal olefins.
Figure 4:
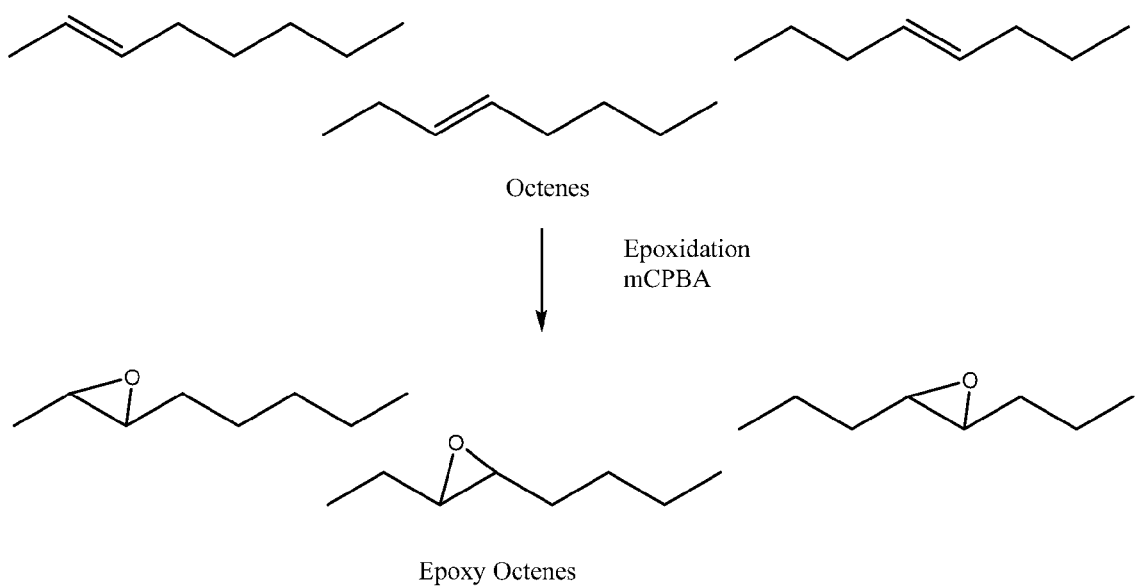
FIG. 4 (Scheme 2) is a chemical flow diagram illustrating the epoxidation step of Example 1 in monoester preparation.

As an example of the above-described isomerizing and as indicated in Scheme 1 (FIG. 3), alpha olefins (α-olefins) can be isomerized to the corresponding internal olefins. In one embodiment, these alpha olefins can be derived from a Fischer-Tropsch process. These internal olefins are then epoxidized, as illustrated in Scheme 2 (FIG. 4). The epoxides can then be transformed to the corresponding secondary mono alcohols via epoxide ring reduction followed by esterifying (i.e., di-esterification) with the appropriate carboxylic acids or their acylating derivatives. It is typically necessary to convert alpha olefins to internal olefins because monoesters of alpha olefins, especially short chain alpha olefins, tend to be solids or waxes. "Internalizing" alpha olefins followed by transformation to the monoester functionalities introduces branching along the chain in the produced esters and thus reduces the symmetry of the molecules, which in turn reduces the pour point of the intended products. Internalizing the ester may also enhance the oxidative and hydrolytic stability. Internal esters show surprising hydrolytic and oxidative stabilities that are much superior to those of terminal esters. Internalizing the ester makes it sterically more hindered, which may contribute to the oxidative and hydrolytic stabilities.

The ester groups with their polar character would further enhance the viscosity of the final product. Branching, introduced by internalizing the ester groups, will enhance the cold temperature properties, such as pour and cloud points. Viscosity can be increased by increasing the carbon number of the internal olefin or the acid used in the esterification.

Regarding the step of epoxidizing (i.e., the epoxidation step), in some embodiments, the above-described olefin (preferably an internal olefin) can be reacted with a peroxide (e.g., $H_2O_2$) or a peroxy acid (e.g., peroxyacetic acid) to generate an epoxide. See, e.g., D. Swern, in *Organic Peroxides Vol. II*, Wiley-Interscience, New York, 1971, pp. 355-533; and B. Plesnicar, in Oxidation in *Organic Chemistry, Part C*, W. Trahanovsky (ed.), Academic Press, New York 1978, pp. 221-253. Olefins can be efficiently transformed to the corresponding diols by highly selective reagent such as osmium tetra-oxide (M. Schroder, Chem. Rev. vol. 80, p. 187, 1980) and potassium permanganate (Sheldon and Kochi, in Metal-Catalyzed Oxidation of Organic Compounds, pp. 162-171 and 294-296, Academic Press, New York, 1981).

Figure 5:
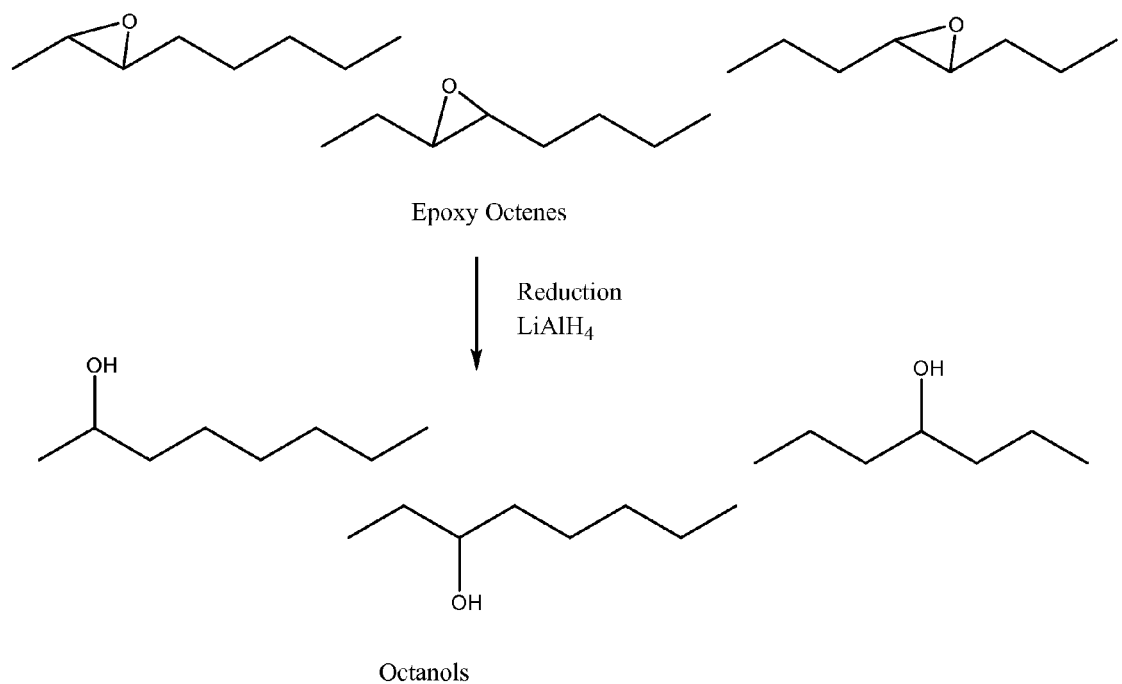
FIG. 5 (Scheme 3) is a chemical flow diagram illustrating, in monoester preparation, the epoxide ring opening step (reduction) to create an alcohol of Example 2.

Regarding the step of epoxide ring opening to the corresponding secondary mono alcohols, this step is done by epoxide ring reduction using metal hydrides reduction procedures or noble metal-catalyzed hydrogenations processes (illustrated in Scheme 3, FIG. 5). Both procedures are very effective at making the needed secondary alcohols for internal epoxides.

Figure 6:
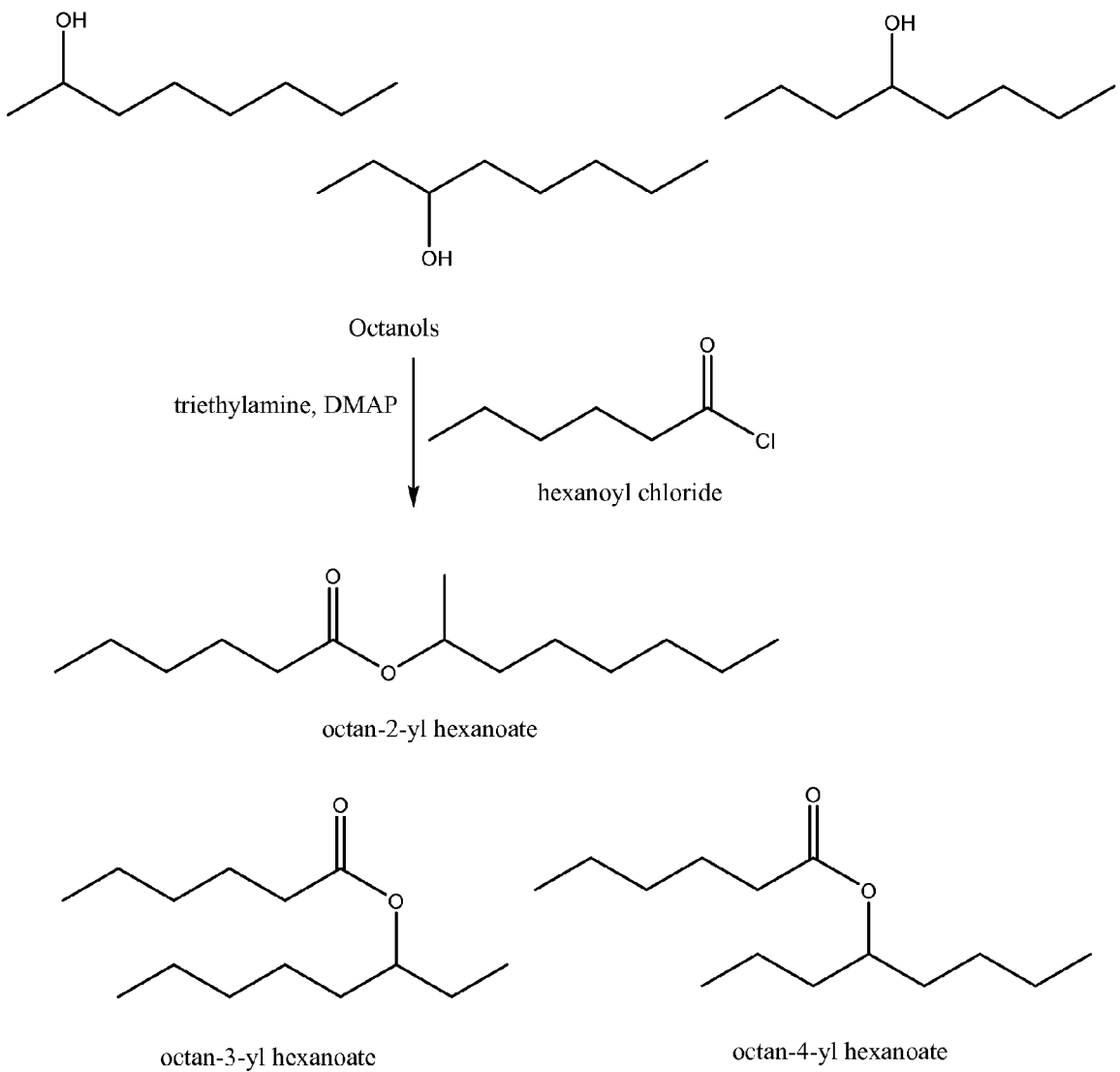
FIG. 6 (Scheme 4) illustrates esterification of octanols with hexanoyl chloride for the synthesis of octyl hexanoates.

Regarding the step of esterifying (esterification), an acid is typically used to catalyze the esterification reaction of alcohols and carboxylic acids (illustrated in Scheme 4, FIG. 6). Suitable acids for esterification include, but are not limited to, sulfuric acid (Munch-Peterson, Org. Synth., V, p. 762, 1973), sulfonic acid (Allen and Sprangler, Org Synth., III, p. 203, 1955), hydrochloric acid (Eliel et al., Org Synth., IV, p. 169, 1963), and phosphoric acid (among others). In some embodiments, the carboxylic acid used in this step is first converted to an acyl chloride (via, e.g., thionyl chloride or $PCl_3$). Alternatively, an acyl chloride could be employed directly. Wherein an acyl chloride is used, an acid catalyst is not needed and a base such as pyridine, 4-dimethylaminopyridine (DMAP) or triethylamine (TEA) is typically added to react with an HCl produced. When pyridine or DMAP is used, it is believed that these amines also act as a catalyst by forming a more reactive acylating intermediate. See, e.g., Fersh et al., J. Am. Chem. Soc., vol. 92, pp. 5432-5442, 1970; and Hofle et al., Angew. Chem. Int. Ed. Engl., vol. 17, p. 569, 1978.

Regardless of the source of the olefin, in some embodiments, the carboxylic acid used in the above-described method is derived from biomass. In certain embodiments, this involves the extraction of some oil (e.g., triglyceride) component from the biomass and hydrolysis of the triglycerides of which the oil component is comprised so as to form free carboxylic acids. In other embodiments, the carboxylic acid is derived from a Fischer-Tropsch process.

Using a synthetic strategy in accordance with that outlined in Scheme 1 (FIG. 3), Scheme 2 (FIG. 4), Scheme 3 (FIG. 5), and Scheme 4 (FIG. 6), a mixture of internal octenes was converted to the corresponding mixture of internal monoester derivatives, octyl hexanoates and octyl decanoates via acylation of the octyl alcohols intermediates with hexanoyl and decanoyl chlorides, respectively. The Examples below explain this process in more detail. Octyl and decyl hexanoates are particularly suitable for use in drilling fluid compositions.

5. Variations

Variations (i.e., alternate embodiments) on the above-described lubricant compositions include, but are not limited to, utilizing mixtures of isomeric olefins and or mixtures of olefins having a different number of carbons. This leads to an isomeric mixture of multiple monoester species in the product compositions.

Variations on the above-described processes include, but are not limited to, using carboxylic acids derived from FT alcohols by oxidation.

6. Examples

The following examples are provided to demonstrate particular embodiments of the present invention. It should be appreciated by those of skill in the art that the methods disclosed in the examples which follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

As an exemplary synthetic procedure, the synthesis of a monoester, octyl hexanoate is described in Examples 1-3. This procedure is representative for making monoesters from internal olefins and carboxylic acid chlorides (acyl chlorides), in accordance with some embodiments of the present invention.

Example 1

This Example serves to illustrate synthesis of a secondary alcohol en route to synthesis of a monoester species, in accordance with some embodiments of the present invention.

Epoxidation of Octenes into Epoxy Octanes

A mixture of 2-octene, 3-octene and 4-octene (1:1:1 mixture), purchased from Aldrich Chemical company, were epoxidized as follows using the general procedure described below (Scheme 1). To a stirred solution of 509 grams (2.95 mol) of 77% mCPBA (meta-chloroperoxybenzoic acid) in 2000 mL n-hexane in an ice bath, 265 grams (2.36 mol) of 2-octene, 3-octene and 4-octene (1:1:1) mixture were added drop-wise via an addition funnel over a period of 60 minutes. The resulting reaction mixture was stirred over 0° C. for 2 hrs. Then, the ice bath was removed and the reaction was allowed to stir overnight. The resulting milky solution was subsequently filtered to remove meta-chloro-benzoic acid that formed therein. The filtrate was then washed with a 10% aqueous solution of sodium bicarbonate. The organic layer was dried over anhydrous magnesium sulfate while stirring for 1 hr. The organic solvent (n-hexane) was removed by distillation at atmospheric pressure and 67-71° C. IR and NMR analysis and GCMS spectroscopy on the remaining solution confirmed the presence of the epoxide mixture with little residual n-hexane. This solution was used as is for next step (reduction of the epoxides to the corresponding secondary alcohols) without any further attempt to remove the remaining hexane. The epoxide is somewhat volatile. Care must be taken to prevent any appreciable loss by distillation or condensation on a rotary evaporator.

Epoxidation was also accomplished using formic acid/hydrogen epoxide solution of 1:1.5 parts.

Example 2

Reduction of 2,3-Epoxy Octanes to Secondary Octanols

Synthesis Examples

The epoxy octanes with little residual hexane produced according to Example 1 were reduced with lithium aluminum hydride in THF (Tetrahydrofuran) according to the procedure described below.

The products from Example 1 were divided into two equal portions and each portion was reduced separately with lithium aluminum hydride in anhydrous THF. Assuming full conversion of the octenes to epoxides in Example 1, each portion was assumed to contain 1.18 moles (151.3 grams) of epoxy octanes. Accordingly, a suspension of 56 grams (1.48 mol.) of lithium aluminum hydride in 1000 mL anhydrous THF in 3-liter 3-neck reaction flask equipped with an overhead stirrer and reflux condenser, was cooled down to 0° C. in an ice-bath. To this suspension and while stirring, one of the two portions of the epoxy octanes mixture (presuming 151.3 grams; 1.18 mol.) was added drop-wise via a sealed dropping funnel. Once the addition was complete, an additional 100 ml of THF was added via the dropping funnel. The reaction mixture was left to stir at 0° C. for 2 hrs. The ice-bath was then removed and the reaction left to stir overnight. The reaction was then heated to reflux for an hour or so to ensure reduction completion. The reaction progress was monitored by NMR and IR analysis on small aliquots work-up. Once completed, the heat source was replaced with an ice-bath and the reaction was worked up by first diluting with 500 ml THF and then adding 550 ml of 15% NaOH solution via a dropping funnel with vigorous stirring and not allowing the temperature of the reaction to rise above room temperature (very slow addition). The addition continued until all the grey solution transformed into a milky solution which was left to stir for addition 30 minutes. The stirring was stopped and the solution separated into a clear liquid phase and a fine white precipitate. The mixture was filtered and the filtrate was dried over anhydrous $MgSO_4$ and then concentrated on a rotary evaporator to remove the solvent THF and afford a mixture of 2-octanol, 3-octanol, and 4-octanol as colorless viscous oil that turned into a very soft waxy substance while standing at room temperature for few days. The reduction afforded 132 grams of the alcohols or 86% yield for the two reactions described in Examples 1 and 2. Reduction of the second portion of the epoxy octanes gave similar results with 84% overall yield.

Reduction was also accomplished by mild hydrogenation over Pd/C catalyst on small scale, as depicted in Scheme 3 (see FIG. 5).

Aside from metal hydrides reductions, the epoxies were also reduced with quantitative yields by mild hydrogenation processes using Pt-based and Pd-based hydrogenation catalysts at 100-150 PSI hydrogen pressure and temperature of 35-50° C.

Example 3

Esterification of Octanols with Hexanoyl Chloride

Synthesis of Octyl Hexanoates

The mixture of 2-octanol, 3-octanol, and 4-octanol prepared in Example 2 was esterified according to the procedure below using hexanoyl chloride as the esterification agent as shown in Scheme 3. To a solution of 130.5 grams (1 mol.) of the octanols mixture in 1000 ml cyclohexane in a 3-neck 3 L round bottom reaction vessel equipped with an overhead stirrer and reflux condenser, 126.5 grams (1.25 mol.) of triethylamine and 6.5 grams (0.05 mol.) of 4-N,N-dimethylaminopyridine (DMAP). The mixture was cooled down by means of an ice-bath and left to stir at around 0° C. for 15 minutes. To the stirring cold solution, 148 grams (1.1 mol.) of hexanoyl chloride was added drop-wise via a dropping funnel over 45 minutes. Once all hexanoyl chloride was added, the reaction was left to stir and warm slowly to room temperature. The reaction, then, was refluxed and monitored by NMR and IR analysis. Once the reaction was completed, the resulting milky creamy solution was worked up by adding water until all the solids disappeared and a clear solution formed (two phase solution). The two phase solution was separated in a separatory funnel and the organic phase was washed with water and brine and saved. The aqueous phase was extracted with ethyl acetate. The ethyl acetate extract was washed with brine and was combined to the organic phase. The organic phase, containing the esters, was dried over anhydrous $MgSO_4$, filtered and concentrated on a rotary evaporator to give 218 grams (96% yields) of the esters mixture as slightly orange-colored oil. The product was passed through 15 cm×5 cm silica gel plug and flushed with hexane. The hexane was removed on a rotary evaporator to give the product as colorless oil (214 gm were recovered).

Using identical synthesis procedures, decyl hexanoates were synthesized in similar yields.

Example 4

Esterification with Hexanoic Acid Using $H_2PO_4$ as Catalyst

The mixture of octanols was also esterified with hexanoic acid in toluene and using phosphoric acid as catalyst according to the procedure shown below. The reaction apparatus consisted of a 3-neck 1 L reaction flask equipped with an overhead stirrer, reflux condenser with a Dean-Stark trap and a heating mantle. The reaction vessel was charged with 50 gm (0.38 mol.) of octanols mixture, 66 gm (0.57 mol.) hexanoic acid, 5 gm of 85% phosphoric acid, and 250 ml toluene. The mixture was heated at reflux (~110° C.) for 6 hrs and left to stir at reflux overnight. One more gram of 85% H3PO4 was added and the reaction was left to continue stirring at reflux until no more water formation was observed (as indicated by the level of water collected in the Dean-Stark trap). In all, the reaction stirred for approximately 36 hrs. The reaction was then cooled down and worked up by removing the toluene on a rotary evaporator followed by extraction in diethyl ether and extensive washing with warm water (4×500 ml) followed by rinsing with 300 ml of saturated sodium bicarbonate solution to remove any residual acids (organic and inorganic) and with brine solution (300 ml). The ether extract was dried over anhydrous $MgSO_4$, filtered and concentrated on a rotary evaporated to remove ether. The reaction afforded 76 gram of faint yellow oil. The oil was then passed through a 10 cm×4 cm silica gel plug to remove any residual acids. After the final purification step, 73 grams of the desired esters (octyl hexanoates) was recovered as colorless oil with a sweet odor.

Example 5

The procedure described in Example 4 was repeated but at a 2 liter scale and 2 gallons of the octyl hexanoates were produced using this scale in few syntheses.

Example 6

Lubrication Properties of Octyl Hexanoates

Table I below shows the lubrication properties of octyl hexanoates and decyl hexanoates. Both of these esters are particularly suitable for use in drilling fluids.

TABLE I

Lubrication Properties of Octyl Hexanoates and Decyl Hexanoates

| Esters | Viscosity @100° C. | Viscosity @40° C. | Viscosity @0° C. | Pour Point ° C. | Oxidator BN |
|---|---|---|---|---|---|
| Octyl Hexanoates | 0.9 cSt. | 2.2 cSt. | 5.8 cSt. | <−60 | 64 hrs |
| Decyl Hexanoates | 1.2 cSt. | 3.1 cSt. | 10.8 cSt. | <−60 | na |

Example 7

Oxidator BN Test

The octyl hexanoate isomeric mixture was evaluated for oxidation stability by measuring how much time it takes for a given amount of the ester to absorb 1 liter of Oxygen using the Oxidator BN test. Octyl hexanoates exhibited superior oxidation stability with 64 hrs (see Tables 1 and 2, FIGS. 7(A) and 7(B)). For comparison, Table II below provides comparative Oxidator BN information for other lubricants, including commercially available lubricants.

TABLE II

Comparative Oxidator BN Data

| Lubricant | Oxidator BN (hours) |
|---|---|
| Group I lubricants | 7.2 |
| Group III | 41.2 |
| Diesters tetradecyl-dilaureate | 26 |
| Diester hexadecyl-dilaureate | 38 |
| Cargill Agri-Pur 75 | 0.17* |
| Cargill Agri-Pur 82 | 0.3* |
| Cargill Agri-Pur 560 | 0.41* |

The Cargill products are commercial ester biolubricants.*

This comparative Oxidator BN data illustrates the superior results obtained for oxidation stability of the octyl hexanoates.

As described herein, the monoester species exhibits superior Oxidator BN values of from about 25 hours to about 80 hours, and in some embodiments, Oxidator BN values of from about 25 hours to about 75 hours. The lubricants comprising the isomeric mixture of at least one monoester species exhibits Oxidator BN values of from about 25 hours to about 65 hours.

7. Summary

In summary, the present invention provides for monoester-based lubricant compositions. The present invention also provides for methods (processes) of making these and other similar lubricant compositions. In some embodiments, the methods for making the monoester-based lubricants utilize a biomass precursor and/or low value Fischer-Tropsch olefins and/or alcohols so as to produce high value monoester-based lubricants. In some embodiments, the monoester-based lubricants are derived from FT olefins and fatty acids. The fatty acids can be from a bio-based source (i.e., biomass, renewable source) or can be derived from FT alcohols via oxidation.

All patents and publications referenced herein are hereby incorporated by reference to the extent not inconsistent herewith. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed is:

1. A lubricant composition comprising an isomeric mixture of at least one monoester species, the monoester species being a secondary monoester and having the following structure:

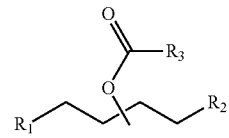

wherein $R_3$ is an alkyl group having a carbon number of from $C_5$ to $C_{14}$ and $R_1$, $R_2$, and $R_3$ are independently selected from alkyl groups to provide a monoester species or mixture of monoester species having a total carbon number up to $C_{40}$, wherein the isomeric mixture of at least one monoester species has an Oxidator BN value of from about 25 hours to about 65 hours.

2. The lubricant composition of claim 1, wherein $R_1$, $R_2$, and $R_3$ are independently selected from alkyl groups to provide a monoester species or mixture of monoester species having a carbon number ranging from $C_{12}$ to $C_{18}$.

3. The lubricant composition of claim 1, wherein $R_1$, $R_2$, and $R_3$ are independently selected from alkyl groups to provide a monoester species or mixture of monoester species having a carbon number ranging from $C_{12}$ to $C_{16}$.

4. The lubricant composition of claim 1, wherein $R_1$ and $R_2$ are independently selected from alkyl groups to have a combined carbon number of $C_6$ to $C_{22}$.

5. The lubricant composition of claim 1, wherein $R_1$ and $R_2$ are independently selected from alkyl groups to have a combined carbon number of $C_4$ to $C_{14}$.

6. The lubricant composition of claim 1, wherein $R_1$ and $R_2$ are independently selected from alkyl groups to have a combined carbon number of $C_4$ to $C_8$ and $R_3$ is an alkyl group having a carbon number of from $C_5$ to $C_{10}$.

7. The lubricant composition of claim 1, wherein the lubricant comprises an isomeric mixture of 2 or more monoester species.

8. The lubricant composition of claim 1, wherein the lubricant comprises an isomeric mixture of 1 to 100 monoester species.

9. The lubricant composition of claim 1, wherein the kinematic viscosity of the composition at a temperature of 100° C. is in the range of 0.5 cSt to 2 cSt.

10. The lubricant composition of claim 1, wherein the pour point is −20° C. or less.

11. The lubricant composition of claim 1, wherein the at least one monoester species is selected from the group consisting of octyl hexanoate, decyl hexanoate, and mixtures thereof.

12. The lubricant composition of claim 1, further comprising a base oil selected from the group consisting of Group I base oils, Group II base oils, Group III base oils, and mixtures thereof.

13. The lubricant composition of claim 1, wherein $R_1$ and $R_2$ are derived from an isomeric mixture of olefins and $R_3$ is derived from a carboxylic acid.

14. The lubricant composition of claim 13, wherein $R_1$ and $R_2$ are derived from a $C_6$ to $C_{22}$ olefin.

* * * * *

UNITED STATES PATENT AND TRADEMARK OFFICE
CERTIFICATE OF CORRECTION

PATENT NO.        : 9,115,326 B2                             Page 1 of 1
APPLICATION NO.   : 14/279027
DATED             : August 25, 2015
INVENTOR(S)       : Saleh Ali Elomari et al.

It is certified that error appears in the above-identified patent and that said Letters Patent is hereby corrected as shown below:

On Title Page, item (60), the Related U.S. Application Data is incorrectly shown as "Provisional application No. 13/682,542, filed on Nov. 20, 2012" and should be corrected as follows On Title Page, item -- (63) Continuation-in-Part application No. 13/682,542, filed on Nov. 20, 2012 --.

Signed and Sealed this
Fifteenth Day of March, 2016

Michelle K. Lee
*Director of the United States Patent and Trademark Office*